United States Patent
Hwang et al.

(12) 
(10) Patent No.: US 6,387,684 B1
(45) Date of Patent: *May 14, 2002

(54) TOPOISOMERASE 1-MEDIATED DNA DELIVERY

(75) Inventors: Jaulang Hwang; Cho-Fat Hui, both of Taipei; Tzong-Yueh Chen, Tainan, all of (TW)

(73) Assignee: Academia Sinica, Taipei (TW)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/395,689

(22) Filed: Sep. 13, 1999

(51) Int. Cl.$^7$ ............................ C12N 9/90; C07K 14/00; C07K 14/21
(52) U.S. Cl. ................ 435/233; 435/183; 530/300; 530/350; 536/23.7
(58) Field of Search ................................ 530/350, 300; 536/23.4, 23.7; 435/183, 233

(56) References Cited

U.S. PATENT DOCUMENTS 5,668,255 A    9/1997   Murphy ...................... 530/350

FOREIGN PATENT DOCUMENTS

WO    WO 94/04696    * 3/1994

OTHER PUBLICATIONS

Hwang et al. Development of a DNA delivery system using Pseudomonas exotoxin A and a DNA binding region of human DNA topoisomerase I, Cancer Gene Therapy 5 (6): Supp; O27–Abstract, Dec. 1998.*

Redinbo et al. Crystal Structures of Human Topoisomerase I in Covalent and Noncovalent Complexes with DNA, Science 279: 1504–1513, Mar. 1998.*

Allured et al., "Structure of Exotoxin a of Pseudomonas Aeruginosa at 3.0–Angstrom Resolution", Proc. Natl. Acad. Sci. USA 83:1320–1324, 1986.

Alsner et al., "Identification of an N–terminal Domain of Eukaryotic DNA Topoisomerase I Dispensable for Catalytic Activity but Essential for in Vivo Function", Journal Biological Chemistry 267:12408–12411, 1992.

Chow et al., "Identification of the Carboxyl–terminal Amino Acids Important for the ADP–Ribosylation Activity of Pseudomonas Exotoxin A", The Journal of Biological Chemistry 264:18818–18823, 1989.

Fominaya et al., "Target Cell–specific DNA Transfer Mediated by a Chimeric Multidomain Protein", The Journal of Biological Chemistry 271:10560–10568, 1996.

Hwang et al., "Functional Domains of Pseudomonas Exotoxin Identified by Deletion Analysis of the Gene Expressed in E. Coli", Cell 48:129–136, 1987.

Hwang et al., "Structure and Function Relationship of Pseudomonas Exotoxin A", The Journal of Biological Chemistry 264:2379–2384, 1989.

* cited by examiner

Primary Examiner—Rebecca E. Prouty
Assistant Examiner—Richard Hutson
(74) Attorney, Agent, or Firm—Fish & Richardson P.C.

(57) ABSTRACT

The invention relates to a polypeptide having (1) a ligand domain that specifically binds to a molecule on an external surface of a cell, and (2) a DNA binding domain of a Topoisomerase I. The polypeptide optionally contains a translocation domain to facilitate DNA delivery into a cell.

19 Claims, No Drawings

TOPOISOMERASE 1-MEDIATED DNA DELIVERY

BACKGROUND OF THE INVENTION

Nucleic acid delivery into cells, including the cell nucleus, can be accomplished by viral and non-viral means. For example, retroviruses and adeno-associated viruses are efficient delivery vehicles often used in gene therapy protocols, even though safety concerns over the use of viruses in humans remain. These concerns have prodded the development of non-viral delivery means, such as the use of liposomes to encapsulate nucleic acids. Unfortunately, non-viral delivery vehicles are generally inefficient when compared to viral vectors, due in part to cellular compartmentalization and degradation of the nucleic acid taken up by a cell.

SUMMARY OF THE INVENTION

The invention is based on the discovery of new DNA binding domains within human topoisomerase I (Topo I). These new DNA binding domains can be fused to a ligand domain which binds to a molecule on an external surface of a cell, thereby providing an efficient means of delivering DNA to the cell surface and potentially increasing DNA uptake into the cell. An example of such a ligand domain is a receptor binding domain of a Pseudomonas exotoxin A, which specifically binds to the LDL/$\alpha_2$-microglobulin cell receptor, a prolific cell surface molecule, especially on hepatocytes.

Accordingly, the invention features a fusion polypeptide having (1) a ligand domain that specifically binds to a molecule on an external surface of a cell, and (2) a DNA binding domain of a Topo I. The fusion polypeptide can further include a membrane translocation domain, e.g., a membrane translocation domain of a Pseudomonas exotoxin A to facilitate delivery of the DNA into the target cell. A membrane translocation domain is an animo acid sequence within a polypeptide which facilitates the translocation of the polypeptide from a non-cytosolic compartment (e.g., endosomes) to the cytosol of a cell.

An example of a membrane translocation domain is amino acids 253–364 of *P. aeruginosa* exotoxin A:

lagnpakhdldikptvishrlhfpeggslaaltahqachlpletf trhrqprg-weqleqcgypvqrlvalylaarlswnqvdqvirnala spgsg-gdlgeaireqpeqarla (SEQ ID NO:6).

Examples of Topo I DNA binding domains include the following human Topo I amino acid sequences:

msgdhlhndsqieadfrlndshkhkdkhkdrehrhkehkkekdre kskhsnsehkdsekkhkekektkhkdgssekhkdkhkdrdkekrk eekvrasgdakikkekengfssppqikdepeddgyfvppkedikp lkrprdeddvdykpkkiktedtkkekkrkleeeedgklkkpknkd kdkkvpepdnkkkkpkkeeeqkwkw-weeerypegikwflehkgp vfappyeplpenvkfyydgkvmkl-spkaeevatffakmldheytt keifrknffkdwrkemtneekniitnl-skc (SEQ ID NO:1), nsehkdsekkhkekektkhkdgssekhkdkhkdrdkekrkeekvr asgdakikkekengfssppqikdepeddgyfvppkedikplkrpr deddvdykpkkiktedtkkekkrkleeeedgklkkpknkdkdkkv pepdnkkkkpkkeee (SEQ ID NO:2), keifrknffkdwrkemtneekniitnlskcdftqmsqyfkaqtea rkqm-skeeklkikeenekllkeygfcimdnhkerianfkieppgl frgrgnhp-kmgmlkr (SEQ ID NO:3), and gsikyimlnpssrikgekdwqkyetarrlkkcvdkirnqyredwk skemkvrqravalyfidklalragnekeegetadtvgccslrveh inlh-peldgqeyvvefdflgkdsiryynkvpvekrvfknlqlfme nkqped-dlfdrlntgilnkhlqdlmegltakvfrtynasi (SEQ ID NO:4).

SEQ ID NOs:2–4 represent amino acids 51–200, 271–375, and 422–596 of human Topo I, respectively. SEQ ID NO:1 represents a longer sequence (amino acids 1–300) encompassing one of the identified DNA binding domains described above (amino acids 51–200; SEQ ID NO:2).

A ligand domain suitable for use in the fusion polypeptide of the invention is a receptor binding domain of *P. aeruginosa* exotoxin A (PE), such as amino acids 1–252 of PE:

mhliphwiplvaslgllaggssasaaeeafdlwnecakacvldlk dgvrss-rmsvdpaiadtngqgvlhysmvleggndalklaidnals itsdg-ltirleggvepnkpvrysytrqargswslnwlvpighekp snikvfihel-nagnqlshmspiytiemgdellaklardatffvra hesnemqptlaishagvsvvmaqtqprrekrwsewasgkvlclld pldgvynylaqqrcnlddtwegkiyrv (SEQ ID NO:5).

The invention also includes a nucleic acid encoding one of the fusion polypeptides described above. In addition, the invention includes a method of producing an above-described fusion polypeptide by introducing a nucleic acid of the invention into a cell and expressing the pQlypeptide in the cell. The nucleic acid can be introduced into the cell by any known method, including transfection or viral delivery.

As used herein, a DNA binding domain is an amino acid sequence which binds DNA of any sequence or topology (e.g., binds to both supercoiled and relaxed circular DNA). All domains can be at least 10 amino acids (e.g., at least 20, 50, 100, 150, or 200 amino acids) in length. They can also be less than 1000 amino acids (e.g., less than 900, 750, 600, or 400 amino acids) in length.

A fusion polypeptide of the invention is useful for delivering any nucleic acid (e.g., a DNA vector), regardless of sequence or topology, into a cell, e.g., for integration and/or expression into a cell genome. In general, the various elements or domains of the polypeptide can in any order from the N-terminus to the C-terminus within the polypeptide, as long as the domains remain functional.

Other features or advantages of the present invention will be apparent from the detailed description, and also from the claims.

DETAILED DESCRIPTION OF THE INVENTION

The invention relates to fusion polypeptides containing a DNA binding domain of a human Topo I. Since the DNA binding domain binds DNA of different sequences or topology to a similar degree, the fusion polypeptides are useful for a number of laboratory techniques in which binding of all forms of DNA is beneficial. For example, a fusion polypeptide that contains a DNA binding domain described herein and a ligand for a cell surface receptor can be used to target any DNA molecule to the cell. The receptor binding domain of a *P. aeruginosa* exotoxin A is a suitable ligand for this purpose. Addition of a cellular translocation domain (e.g., the translocation domain of a *P. aeruginosa* exotoxin A) can also be included to further enhance the ability of the fusion polypeptide to deliver DNA into cells.

Without further elaboration, it is believed that one skilled in the art can, based on the above disclosure and the description below, utilize the present invention to its fullest extent. The following example is to be construed as merely illustrative of how one skilled in the art can practice the invention and are not limitative of the remainder of the disclosure in any way. Any publications cited in this disclosure are hereby incorporated by reference.

Construction and characterization of GST-Topo I fusion polypeptides containing deletions. Twenty-one separate deletions plasmids, spanning the Topo I open reading frame, were constructed using human DNA Topo I cDNA as starting material. The constructs were produced by PCR using primers that carried desired restriction sites. PCR products were visualized by staining with ethidium bromide after electrophoresis in 6% polyacrylamide gels. PCR products with correct sizes were electroeluted from the gels and cleaved with restriction enzymes.

Various deletion fragments were subcloned into plasmid pGEX-KG, a glutathione S-transferase (GST) fusion polypeptide expression vector (Hwong et al., J. Biol. Chem. 268:18982–18986, 1993). After insertion, all insert fragments were in-frame with the GST gene, and the junctions confirmed by DNA sequencing.

Expression plasmids encoding the various Topo I mutants were introduced into E. coli DH5α. To express GST fusion polypeptide in large quantities in bacteria, colonies of plasmid-carrying DH5α were pooled and grown in a 2-liter culture. When the cell density of the culture reached $3 \times 10^7$ cells/ml, IPTG was added to a final concentration of 0.5 $\mu$M. Cells were harvested 90 minutes later by centrifugation and resuspended in 25 ml of PBST buffer (140 mM NaCl, 2 mM KCl, 5 mM $Na_2HPO_4$, 2 mM $NaH_2PO_4$, 1% Triton X-100 [pH 8.0]) containing 1 mM phenylmethylsulfonyl-fluoride. The purification procedure is generally described in Chang et al., Diabetes 45:408–414, 1996.

Cells were lysed with lysozyme (1 mg/ml) at 25° C. for 5 minutes. The lysate was centrifuged at 10,000×g for 30 minutes at 4° C., and the supernatant was applied to a glutathione-agarose affinity column. Unbound polypeptides were washed out by PBS buffer. The GST fusion polypeptide was eluted with 50 mM Tris-HCl (pH 8.0) containing 10 mM glutathione. The purity of eluted products was confirmed by running the elution on a 12.5% SDS-PAGE gel.

Purified fusion polypeptides were further characterized using rabbit polyclonal anti-GST serum or rabbit polyclonal anti-human DNA Topo I serum as described in J. Biol. Chem. 267:24034–24040, 1992. Using western blotting, all recombinant human DNA Topo I polypeptides could be recognized by a GST polyclonal antibody (Oncogene Research), as well as a human DNA Topo I polyclonal antibody, which was raised as described in Hwong et al., supra.

To test each of the Topo I deletion mutants, the recombinant polypeptides produced in and purified from bacteria were used in a gel mobility shift assay with a pCMV plasmid as the target. pCMV plasmid DNA (0.5 $\mu$g) and GST-Topo I fusion polypeptides were mixed in 50 mM Tris (pH 7.5) to form 15 $\mu$l reactions. The reactions were incubated for 5 minutes at room temperature, as described in Schneider et al., Nucleic Acids Res. 24:3873–3874, 1996, before loading on a 0.8% agarose gel in TBE buffer. The samples were run at 4.1 V/cm and visualized by staining with ethidium bromide. Reaction conditions for pGEM-βgal plasmid DNA (Promega, 1 $\mu$g) and PE(ΔIII)-TOPN fusion polypeptide or other control polypeptides were similar. The PE(ΔIII)-TOPN fusion polypeptide contains a polyhistidine tag and a P. aeruginosa exotoxin A having a deletion in domain III, which contains the ADP-ribosylation activity.

After electrophoresis of the mixture of pCMV plasmid DNA and PE(ΔIII)-TOPN fusion polypeptide or another control polypeptide, separated samples were transferred to a nitrocellulose membrane, using 0.5×TBE buffer (2.5 mM Tris, 9.2 mM glycine [pH 8.3]), at room temperature for 12 hours. The membrane was incubated with a 1:5000 dilution of anti-PE serum, followed by an incubation with anti-rabbit IgG conjugated to alkaline phosphatase. The secondary antibody was visualized using 5-bromo-4-chloro-3-indolylphosphate (BCIP) and nitro blue tetrazolium (NBT) under standard conditions.

The smallest regions of amino acid sequences that can bind DNA was summarized, and the results demonstrated the existence of at least four DNA binding regions. These four regions correspond to amino acids 51–200, 271–375, 422–596, and 651–696 of human DNA Topo I. The highly conserved core domain (198–650) contains two DNA binding regions, while the relatively variable N-terminal region (1–197) and linker region (651–696) also contain one DNA binding region each. The N-terminal region (3–200) of human DNA Topo I was used to construct the DNA delivery vehicle described below.

Construction and characterization of P. aeruginosa exotoxin/human Topo I fusion polypeptides. Plasmid pJH4, which encodes the full length PE (Hwang et al., Cell 48:129–136, 1987) was used as the starting material to construct various plasmids. There are two AatII sites, one located at the boundary region of domain Ib and domain III of the PE gene, and the other located downstream of the PE gene near the EcoRI site beyond the 3' end. The second AatII site was destroyed by partially cleaving the plasmid pJH4 with AatII, followed by removing the single stranded end with mung bean nuclease and religation with T4 DNA ligase, thereby constructing plasmid pJMx. The AatII site immediately upstream of the domain III of PE was retained, while the other AatII site downstream of the PE gene was removed.

The expression vector pET-15b (Novagen), which contains the T7 promoter followed by a hexahistidine-tag sequence and polylinker, was used for expressing all the recombinant polypeptides in this study. A NdeI-PstI fragment containing the full length PE structural gene obtained from pJMx was subcloned into the corresponding restriction sites of pET-15b. The resulting plasmid, pET15PMx, encodes the full length PE with a N-terminal $(His)_6$-tag.

In pET15PMx, an EcoRI site and a SacII site flank the ADP-ribosylation domain of the exotoxin. A fragment encoding amino acids 3–200 of human Topo I and including EcoRI and SacII sites at its ends was generated by PCR. The PCR product and pET15PMx were digested with EcoRI and SacII and ligated together to produce pPETOPN. This plasmid expressed PE(ΔIII)-TOPN, a recombinant histidine-tagged PE polypeptide in which the ADP-ribosylation domain of PE has been replaced with a DNA binding domain of human Topo I.

Plasmids encoding histidine-tagged fusion polypeptides PE(ΔIII)-TOPN, PE(ΔIII) (amino acids 1–425 of PE), and PE(ΔIII)-GnRH (amino acids 1–413 of PE linked to a single copy of gonadotropin releasing hormone) were introduced into E. coli BL21 (DE3, LysS). Expression of the polypeptides were induced using IPTG. The cells were harvested 90 minutes after IPTG induction and resuspended in 20 ml of 8 M urea for 12 hours. The lysate was centrifuged at 10,000×g for 30 min at 4° C., and the supernatant collected. The supernatant was adjusted with 8× binding buffer to achieve a final solution containing 5 mM imidazole, 0.5 M NaCl, 20 mM Tris-HCl (pH 7.9), and 6 M urea, then applied to a $Ni^{2+}$-affinity column. Unbound polypeptides were washed out with 60 mM imidazole. The histidine-tagged fusion polypeptides were then eluted with 150 mM imidazole. The purified recombinant polypeptides were run on a 12.5% SDS-PAGE gel to confirm nearly homogeneous purity.

The column fractions were dialyzed against 50 mM Tris-HCl (pH 7.5) and then concentrated using a YM-10 filter (Amicom). The identity and purity of the concentrated polypeptides were also confirmed using a 12.5% SDS-PAGE gel.

Each of the above polypeptides were immunoblotted as follows. Polyclonal anti-PE antibody was raised in rabbits as described in Hwang et al., J. Biol. Chem. 264:2379–2384, 1989. Polyclonal anti-human DNA Topo I sera were raised as described in Hwong et al., supra. Samples containing purified human DNA Topo I fusion polypeptides or PE(ΔIII)-TOPN were boiled for 5 minutes prior to loading onto a SDS-PAGE gel. After electrophoresis, polypeptides were transferred to a polyvinylidenedifluoride (PVDF) membrane (Millipore) by electrotransfer in Tris-glycine buffer (2.5 mM Tris, 9.2 mM glycine, pH 8.3) containing 20% methanol, at 20 mA and 4° C. for 4 hours. The membrane was then incubated with 1:5000 dilution of the anti-human DNA Topo I serum or anti-PE serum, followed by application of the secondary antibody, anti-rabbit IgG conjugated to alkaline phosphatase. The secondary antibody was visualized using BCIP and NBT under standard conditions.

PE(ΔIII)-TOPN and control polypeptides PE(ΔIII) and PE(ΔIII)-GnRH were tested for DNA binding ability using a agarose gel mobility shift assay and immunoblotting with anti-PE polyclonal antibody as described above. Starting with 1 mg of supercoiled pGEM-βgal, various amounts of recombinant polypeptide were added. Mobility shift of the pGEM-βgal bands was detected with as little as 1 μg of PE(ΔIII)-TOPN in the binding mixture. Most of the DNA shifted to a slower mobility when the polypeptide amount reached 5 μg, at which point the molar ratio of polypeptide:DNA was about 250:1. However, when BSA, PE, or PE(ΔIII)-GnRH were added to the plasmid, no shift of mobility was observed at any polypeptide amount tested. Intermediate amounts of polypeptide resulted in intermediate degrees of mobility shift. Thus, the DNA mobility shift was specifically caused by DNA binding to the recombinant polypeptide PE(ΔIII)-TOPN.

Use of PE(ΔIII)-TOPN as DNA delivery vehicle into cells. The ability of PE(ΔIII)-TOPN to facilitate DNA delivery into cells was assessed using commonly available cells lines. The human ovarian cancer cell line A2780 was maintained in plastic culture dishes containing RPMI medium supplemented with 10% fetal calf serum. The human cervical carcinoma cell line HeLa and the human hepatoma cell line HepG$_2$- were maintained in plastic culture dishes containing DMEM medium. All cultures were grown at 37° C. and in air supplemented with 5% CO$_2$.

Each well of a 12-well tissue culture plate was seeded with A2780 cells at a density of $2 \times 10^4$ cells per well. The plate was cultured at 37° C. overnight. The cells were then washed with 1×PBS before incubating with a mixture of plasmid DNA and recombinant polypeptide. Five micrograms of PE(ΔIII)-TOPN was mixed with 1 μg of pEGFP-N1, which encodes green fluorescent polypeptide (GFP), in 50 mM Tris-HCl (pH 7.5) for 5 minutes at room temperature. The mixture was then added to 1 ml RPMI medium, before transferring the DNA/polypeptide mixture to a well of A2780 cells. The cells were cultured for 48 hours in air supplemented with 5% CO$_2$, at 37° C. Cells expressing GFP were detected using a ultraviolet light source and a 490 nm filter.

The HeLa and HepG$_2$ cells were seeded at $2 \times 10^4$ cells/well, and the GFP-expressing plasmid was delivered into the cells as described above for A2780 cells.

DNA delivery into each cell line was carried out in triplicate. In each experiment for each cell line, 500 cells were observed for evidence of fluorescence and counted for transfer efficiency. The transfer efficiency for PE(ΔIII)-TOPN was 10±2 cells/500 cells for A2780, and that for a liposome control was 9±2 cells/500 cells for A2780. Results were similar when HeLa and HepG$_2$ cells were tested. Surprisingly, the recombinant polypeptide was just as effective as, if not more effective than, a commercial liposome-based transfection reagent in facilitating DNA delivery into cells.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A polypeptide consisting of, in any order, one or more ligand domains that specifically bind to a molecule on an external surface of a cell; one or more fragments of a Topoisomerase I, each fragment being less than 400 amino acids in length and consisting of an amino acid sequence corresponding to positions selected from the group consisting of 1–300, 51–200, 271–375, 422–596, and 651–696 of a Topoisomerase I; and one or more non-Topoisomerase I amino acid sequences.

2. The polypeptide of claim 1, wherein at least one of the ligand domains is a receptor binding domain of a Pseudomonas exotoxin A.

3. The polypeptide of claim 2, wherein at least one of the one or more non-Topoisomerase I amino acid sequences is a membrane translocation domain of a Pseudomonas exotoxin A.

4. The polypeptide of claim 3, wherein one of the one or more fragments contains SEQ ID NO:1.

5. The polypeptide of claim 3, wherein one of the one or more fragments contains SEQ ID NO:2.

6. The polypeptide of claim 3, wherein one of the one or more fragments contains SEQ ID NO:3.

7. The polypeptide of claim 3, wherein one of the one or more fragments contains SEQ ID NO:4.

8. The polypeptide of claim 3, wherein the receptor binding domain contains SEQ ID NO:5.

9. The polypeptide of claim 1, wherein at least one of the one or more non-Topoisomerase I amino acid sequences is a membrane translocation domain.

10. The polypeptide of claim 9, wherein the translocation domain is a membrane translocation domain of a Pseudomonas exotoxin A.

11. The polypeptide of claim 10, wherein one of the one or more fragments contains SEQ ID NO:1.

12. The polypeptide of claim 10, wherein one of the one or more fragments contains SEQ ID NO:2.

13. The polypeptide of claim 10, wherein one of the one or more fragments contains SEQ ID NO:3.

14. The polypeptide of claim 10, wherein one of the one or more fragments contains SEQ ID NO:4.

15. The polypeptide of claim 10, wherein the membrane translocation domain contains SEQ ID NO:6.

16. The polypeptide of claim 1, wherein one of the one or more fragments contains SEQ ID NO:1.

17. The polypeptide of claim 1, wherein one of the one or more fragments contains SEQ ID NO:2.

18. The polypeptide of claim 1, wherein one of the one or more fragments contains SEQ ID NO:3.

19. The polypeptide of claim 1, wherein one of the one or more fragments contains SEQ ID NO:4.

* * * * *

SEQUENCE LISTING

<160> NUMBER OF SEQ ID NOS: 6

<210> SEQ ID NO 1
<211> LENGTH: 300
<212> TYPE: PRT
<213> ORGANISM: Pseudomonas aeruginosa

<400> SEQUENCE: 1

Met Ser Gly Asp His Leu His Asn Asp Ser Gln Ile Glu Ala Asp Phe
1               5                   10                  15

Arg Leu Asn Asp Ser His Lys His Lys Asp Lys His Lys Asp Arg Glu
            20                  25                  30

His Arg His Lys Glu His Lys Lys Glu Lys Asp Arg Glu Lys Ser Lys

-continued

```
                 35                  40                  45
His Ser Asn Ser Glu His Lys Asp Ser Glu Lys Lys His Lys Glu Lys
         50                  55                  60
Glu Lys Thr Lys His Lys Asp Gly Ser Ser Lys His Lys Asp Lys
 65                  70                  75                  80
His Lys Asp Arg Asp Lys Glu Lys Arg Lys Glu Glu Lys Val Arg Ala
                 85                  90                  95
Ser Gly Asp Ala Lys Ile Lys Lys Glu Lys Glu Asn Gly Phe Ser Ser
                100                 105                 110
Pro Pro Gln Ile Lys Asp Glu Pro Glu Asp Asp Gly Tyr Phe Val Pro
                115                 120                 125
Pro Lys Glu Asp Ile Lys Pro Leu Lys Arg Pro Arg Asp Glu Asp Asp
            130                 135                 140
Val Asp Tyr Lys Pro Lys Lys Ile Lys Thr Glu Asp Thr Lys Lys Glu
145                 150                 155                 160
Lys Lys Arg Lys Leu Glu Glu Glu Asp Gly Lys Leu Lys Lys Pro
                165                 170                 175
Lys Asn Lys Asp Lys Asp Lys Lys Val Pro Glu Pro Asp Asn Lys Lys
                180                 185                 190
Lys Lys Pro Lys Lys Glu Glu Glu Gln Lys Trp Lys Trp Trp Glu Glu
                195                 200                 205
Glu Arg Tyr Pro Glu Gly Ile Lys Trp Lys Phe Leu Glu His Lys Gly
            210                 215                 220
Pro Val Phe Ala Pro Pro Tyr Glu Pro Leu Pro Glu Asn Val Lys Phe
225                 230                 235                 240
Tyr Tyr Asp Gly Lys Val Met Lys Leu Ser Pro Lys Ala Glu Glu Val
                245                 250                 255
Ala Thr Phe Phe Ala Lys Met Leu Asp His Glu Tyr Thr Thr Lys Glu
                260                 265                 270
Ile Phe Arg Lys Asn Phe Phe Lys Asp Trp Arg Lys Glu Met Thr Asn
                275                 280                 285
Glu Glu Lys Asn Ile Ile Thr Asn Leu Ser Lys Cys
            290                 295                 300

<210> SEQ ID NO 2
<211> LENGTH: 150
<212> TYPE: PRT
<213> ORGANISM: Pseudomonas aeruginosa

<400> SEQUENCE: 2

Asn Ser Glu His Lys Asp Ser Glu Lys Lys His Lys Glu Lys Glu Lys
  1               5                  10                  15
Thr Lys His Lys Asp Gly Ser Ser Lys His Lys Asp Lys His Lys
             20                  25                  30
Asp Arg Asp Lys Glu Lys Arg Lys Glu Glu Lys Val Arg Ala Ser Gly
             35                  40                  45
Asp Ala Lys Ile Lys Lys Glu Lys Glu Asn Gly Phe Ser Ser Pro Pro
         50                  55                  60
Gln Ile Lys Asp Glu Pro Glu Asp Asp Gly Tyr Phe Val Pro Pro Lys
 65                  70                  75                  80
Glu Asp Ile Lys Pro Leu Lys Arg Pro Arg Asp Glu Asp Asp Val Asp
                 85                  90                  95
Tyr Lys Pro Lys Lys Ile Lys Thr Glu Asp Thr Lys Lys Glu Lys Lys
                100                 105                 110
```

```
Arg Lys Leu Glu Glu Glu Asp Gly Lys Leu Lys Lys Pro Lys Asn
        115                 120                 125

Lys Asp Lys Asp Lys Lys Val Pro Glu Pro Asp Asn Lys Lys Lys
130                 135                 140

Pro Lys Lys Glu Glu Glu
145                 150

<210> SEQ ID NO 3
<211> LENGTH: 105
<212> TYPE: PRT
<213> ORGANISM: Pseudomonas aeruginosa

<400> SEQUENCE: 3

Lys Glu Ile Phe Arg Lys Asn Phe Phe Lys Asp Trp Arg Lys Glu Met
1               5                   10                  15

Thr Asn Glu Glu Lys Asn Ile Ile Thr Asn Leu Ser Lys Cys Asp Phe
                20                  25                  30

Thr Gln Met Ser Gln Tyr Phe Lys Ala Gln Thr Glu Ala Arg Lys Gln
            35                  40                  45

Met Ser Lys Glu Glu Lys Leu Lys Ile Lys Glu Glu Asn Glu Lys Leu
50                  55                  60

Leu Lys Glu Tyr Gly Phe Cys Ile Met Asp Asn His Lys Glu Arg Ile
65                  70                  75                  80

Ala Asn Phe Lys Ile Glu Pro Pro Gly Leu Phe Arg Gly Arg Gly Asn
                85                  90                  95

His Pro Lys Met Gly Met Leu Lys Arg
            100                 105

<210> SEQ ID NO 4
<211> LENGTH: 175
<212> TYPE: PRT
<213> ORGANISM: Pseudomonas aeruginosa

<400> SEQUENCE: 4

Gly Ser Ile Lys Tyr Ile Met Leu Asn Pro Ser Ser Arg Ile Lys Gly
1               5                   10                  15

Glu Lys Asp Trp Gln Lys Tyr Glu Thr Ala Arg Arg Leu Lys Lys Cys
                20                  25                  30

Val Asp Lys Ile Arg Asn Gln Tyr Arg Glu Asp Trp Lys Ser Lys Glu
            35                  40                  45

Met Lys Val Arg Gln Arg Ala Val Ala Leu Tyr Phe Ile Asp Lys Leu
50                  55                  60

Ala Leu Arg Ala Gly Asn Glu Lys Glu Glu Gly Glu Thr Ala Asp Thr
65                  70                  75                  80

Val Gly Cys Cys Ser Leu Arg Val Glu His Ile Asn Leu His Pro Glu
                85                  90                  95

Leu Asp Gly Gln Glu Tyr Val Val Glu Phe Asp Phe Leu Gly Lys Asp
            100                 105                 110

Ser Ile Arg Tyr Tyr Asn Lys Val Pro Val Glu Lys Arg Val Phe Lys
            115                 120                 125

Asn Leu Gln Leu Phe Met Glu Asn Lys Gln Pro Glu Asp Asp Leu Phe
130                 135                 140

Asp Arg Leu Asn Thr Gly Ile Leu Asn Lys His Leu Gln Asp Leu Met
145                 150                 155                 160

Glu Gly Leu Thr Ala Lys Val Phe Arg Thr Tyr Asn Ala Ser Ile
                165                 170                 175
```

```
<210> SEQ ID NO 5
<211> LENGTH: 252
<212> TYPE: PRT
<213> ORGANISM: Pseudomonas aeruginosa

<400> SEQUENCE: 5

Met His Leu Ile Pro His Trp Ile Pro Leu Val Ala Ser Leu Gly Leu
 1               5                  10                  15

Leu Ala Gly Gly Ser Ser Ala Ala Glu Glu Ala Phe Asp Leu
                20                  25                  30

Trp Asn Glu Cys Ala Lys Ala Cys Val Leu Asp Leu Lys Asp Gly Val
                35                  40                  45

Arg Ser Ser Arg Met Ser Val Asp Pro Ala Ile Ala Asp Thr Asn Gly
     50                  55                  60

Gln Gly Val Leu His Tyr Ser Met Val Leu Glu Gly Gly Asn Asp Ala
 65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
               100                 105                 110

Ser Tyr Thr Arg Gln Ala Arg Gly Ser Trp Ser Leu Asn Trp Leu Val
               115                 120                 125

Pro Ile Gly His Glu Lys Pro Ser Asn Ile Lys Val Phe Ile His Glu
   130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
               165                 170                 175

Phe Val Arg Ala His Glu Ser Asn Glu Met Gln Pro Thr Leu Ala Ile
               180                 185                 190

Ser His Ala Gly Val Ser Val Val Met Ala Gln Thr Gln Pro Arg Arg
   195                 200                 205

Glu Lys Arg Trp Ser Glu Trp Ala Ser Gly Lys Val Leu Cys Leu Leu
   210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val
               245                 250

<210> SEQ ID NO 6
<211> LENGTH: 112
<212> TYPE: PRT
<213> ORGANISM: Pseudomonas aeruginosa

<400> SEQUENCE: 6

Leu Ala Gly Asn Pro Ala Lys His Asp Leu Asp Ile Lys Pro Thr Val
 1               5                  10                  15

Ile Ser His Arg Leu His Phe Pro Glu Gly Gly Ser Leu Ala Ala Leu
                20                  25                  30

Thr Ala His Gln Ala Cys His Leu Pro Leu Glu Thr Phe Thr Arg His
                35                  40                  45

Arg Gln Pro Arg Gly Trp Glu Gln Leu Glu Gln Cys Gly Tyr Pro Val
     50                  55                  60

Gln Arg Leu Val Ala Leu Tyr Leu Ala Ala Arg Leu Ser Trp Asn Gln
 65                  70                  75                  80
```

―continued

```
Val Asp Gln Val Ile Arg Asn Ala Leu Ala Ser Pro Gly Ser Gly Gly
            85                  90                  95

Asp Leu Gly Glu Ala Ile Arg Glu Gln Pro Glu Gln Ala Arg Leu Ala
            100                 105                 110
```